(12) United States Patent
Ravishankar et al.

(10) Patent No.: US 11,972,593 B2
(45) Date of Patent: Apr. 30, 2024

(54) SYSTEM AND METHODS FOR QUANTIFYING UNCERTAINTY OF SEGMENTATION MASKS PRODUCED BY MACHINE LEARNING MODELS

(71) Applicant: GE Precision Healthcare LLC, Milwaukee, WI (US)

(72) Inventors: Hariharan Ravishankar, Karnataka (IN); Pavan Annangi, Karnataka (IN)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 259 days.

(21) Appl. No.: 17/453,319

(22) Filed: Nov. 2, 2021

(65) Prior Publication Data
US 2023/0135351 A1 May 4, 2023

(51) Int. Cl.
*G06T 7/77* (2017.01)
*A61B 5/00* (2006.01)
(Continued)

(52) U.S. Cl.
CPC .............. *G06T 7/77* (2017.01); *A61B 5/1079* (2013.01); *A61B 5/7267* (2013.01); *A61B 5/742* (2013.01);
(Continued)

(58) Field of Classification Search
CPC ......... G06T 2207/20081; G06T 7/0012; G06T 2207/10132; G06T 2207/20084;
(Continued)

(56) References Cited

U.S. PATENT DOCUMENTS 10,893,849 B2 1/2021 Satoh et al.
10,937,155 B2 3/2021 McLeod
(Continued)

FOREIGN PATENT DOCUMENTS

WO 2019176449 A1 9/2019

OTHER PUBLICATIONS

Wang, Guotai, et al. "Aleatoric uncertainty estimation with test-time augmentation for medical image segmentation with convolutional neural networks." Neurocomputing 338 (2019): 34-45. (Year: 2019).*
(Continued)

*Primary Examiner* — Phi Hoang
*Assistant Examiner* — Scott E Sonners
(74) *Attorney, Agent, or Firm* — McCoy Russell LLP

(57) ABSTRACT

Systems and methods are provided for quantifying uncertainty of segmentation mask predictions made by machine learning models, where the uncertainty may be used to streamline an anatomical measurement workflow by automatically identifying less certain caliper placements. In one example, the current disclosure teaches receiving an image including a region of interest, determining a segmentation mask for the region of interest using a trained machine learning model, placing a caliper at a position within the image based on the segmentation mask, determining an uncertainty of the position of the caliper, and responding to the uncertainty of the position of the caliper being greater than a pre-determined threshold by displaying a visual indication of the position of the caliper via a display device and prompting a user to confirm or edit the position of the caliper.

13 Claims, 5 Drawing Sheets

(51) Int. Cl.
  *A61B 5/107* (2006.01)
  *G06T 7/11* (2017.01)
  *G06T 7/73* (2017.01)
  *G06T 11/00* (2006.01)
(52) U.S. Cl.
  CPC .............. *A61B 5/7475* (2013.01); *G06T 7/11* (2017.01); *G06T 7/73* (2017.01); *G06T 11/00* (2013.01); *G06T 2200/24* (2013.01); *G06T 2207/20081* (2013.01); *G06T 2207/20084* (2013.01); *G06T 2207/20104* (2013.01); *G06T 2207/30004* (2013.01); *G06V 2201/034* (2022.01)
(58) Field of Classification Search
  CPC .................. G06T 2200/24; G06T 7/73; G06T 2207/10088; G06T 2207/10116; G06T 2207/30004; G06T 2207/30168; G06T 7/11; G06T 11/00; G06T 7/0002; G06T 7/12; G06T 2207/20061; G06T 2207/20076; G06T 2207/20092; G06T 2207/20104; G06T 2207/20132; G06T 7/001; G06T 7/10; G06T 7/13; G06T 7/33; G06T 7/62; A61B 8/5223; A61B 8/469; A61B 8/085; A61B 8/467; A61B 5/7267; A61B 5/742; A61B 5/743; G16H 30/40; G06V 10/82; G06V 10/764; G06V 10/809; G06V 2201/03; G06V 10/44; G06F 18/24155
  See application file for complete search history.

(56) References Cited

U.S. PATENT DOCUMENTS 11,036,376 B2    6/2021  Tashiro et al.
2020/0345331 A1* 11/2020  Ebata .................... A61B 8/467

OTHER PUBLICATIONS

Gal, Y. et al., "Dropout as a Bayesian Approximation: Representing Model Uncertainty in Deep Learning," arXiv Cornell University Website, Available Online at https://arxiv.org/abs/1506.02142, Available as Early as Jun. 6, 2015, 12 pages.

Ayhan, P. et al., "Test-time Data Augmentation for Estimation of Heteroscedastic Aleatoric Uncertainty in Deep Neural Networks," Proceedings of the 2018 Medical Imaging with Deep Learning, Jul. 4, 2018, Amsterdam, 9 pages.

Wang, G. et al., "Aleatoric uncertainty estimation with test-time augmentation for medical image segmentation with convolutional neural networks," arXiv Cornell University Website, Available Online at https://arxiv.org/abs/1807.07356, Available as Early as Jul. 19, 2018, 13 pages.

Kana, M. et al., "Uncertainty in Deep Learning. How to Measure? A hands-on tutorial on Bayesian estimation of epistemic and aleatoric uncertainty with Keras. Towards a social acceptance of AI.," Towards Data Science Website, Available Online at https://towardsdatascience.com/my-deep-learning-model-says-sorry-i-dont-know-the-answer-that-s-absolutely-ok-50ffa562cb0b, Apr. 26, 2020, 24 pages.

* cited by examiner

SYSTEM AND METHODS FOR QUANTIFYING UNCERTAINTY OF SEGMENTATION MASKS PRODUCED BY MACHINE LEARNING MODELS

TECHNICAL FIELD

Embodiments of the subject matter disclosed herein relate to medical imaging, and more particularly, to determining uncertainty of segmentation masks produced from medical images.

BACKGROUND

Machine learning models are routinely employed in the field of medical image processing and medical image analysis. In one example, machine learning models may be used to segment a medical image into different anatomical regions, or other regions of interest, by predicting/inferring one or more segmentation masks for the regions of interest, wherein a segmentation mask identifies pixels/voxels of an input image belonging to a particular region of interest. One recognized limitation of the segmentation masks produced via machine learning models is the inability to distinguish between more and less confident segmentation masks, or between more and less confident regions within a segmentation mask. In conventional approaches, uncertainty of a machine learning model's predictions is quantified during a training phase (e.g., accuracy, precision, recall, cross-entropy etc.), and thus a same uncertainty may be associated with segmentation masks produced by a particular machine learning model, regardless of the quality or identity of the input image. Therefore, in conventional approaches, it may be difficult for a user to determine if the information presented by a segmentation mask, or derived therefrom, should be accepted or rejected. In particular, in anatomical measurement workflows, or other workflows where a position of an anatomical landmark or other feature may be automatically determined based on output from a machine learning model (e.g., a segmentation mask), it may be difficult to accurately assess the certainty/confidence of the automatically determined landmark position. In such cases, a radiologist or other user may need to manually evaluate each automatically determined position before proceeding, thereby reducing the efficiency of medical imaging workflows. Therefore, exploring approaches for automatically determining anatomical landmark position certainty/confidence is generally desired.

SUMMARY

The present disclosure at least partially addresses the issues described above. In one embodiment, the efficiency of an imaging workflow may be increased by automatically identifying uncertain caliper positions by, receiving an image including a region of interest, determining a segmentation mask for the region of interest using a trained machine learning model, placing a caliper at a position within the image based on the segmentation mask, determining an uncertainty of the position of the caliper based on an uncertainty of the segmentation mask, and responding to the uncertainty of the position of the caliper being greater than a pre-determined threshold by displaying a visual indication of the position of the caliper via a display device and prompting a user to confirm or edit the position of the caliper. As a non-limiting example, the uncertainty of the segmentation mask may be determined by producing a plurality of segmentation masks from a plurality of distinctly augmented versions of the received image, and generating an uncertainty map showing the spatial distribution of segmentation label uncertainty by encoding the per-pixel segmentation label variation across the plurality of segmentation masks. In this way, caliper placement uncertainty may be automatically estimated, and used to streamline an imaging workflow by prompting a user to confirm or edit caliper placements with greater than a threshold of uncertainty, and not prompting a user to confirm or edit caliper placements with less than the threshold of uncertainty.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

Figure 1:
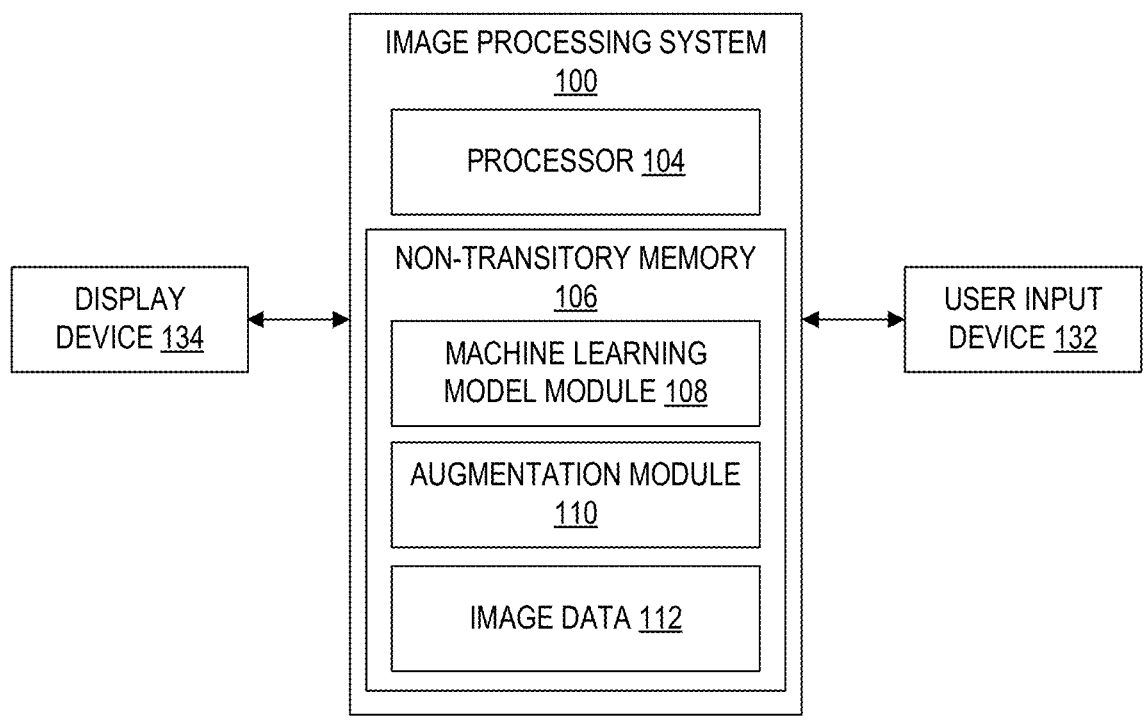
FIG. 1 is a schematic diagram illustrating a system for determining segmentation masks and uncertainty maps for medical images.

The drawings illustrate specific aspects of the described systems and methods for quantifying uncertainty of segmentation masks produced by machine learning models. Together with the following description, the drawings demonstrate and explain the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

The following description relates to various embodiments for quantifying uncertainty of segmentation masks produced by machine learning models, and using said uncertainty to streamline medical imaging workflows. In one example, a medical imaging workflow includes measurement of an anatomical region of interest based on positions of one or more calipers, wherein the positions of the calipers may be determined based on a segmentation mask of the anatomical region of interest. In some embodiments, an image processing system, such as image processing system 100 shown in FIG. 1 may receive a medical image including a region of interest. The image processing system may execute a method, such as method 200 shown in FIG. 2 to segment the region of interest, and quantify the uncertainty associated with location and extent of the segmented region of interest. In some embodiments, method 200 includes augmenting the medical image by applying one, or a combination of, augmentations to produce a plurality of augmented images. Non-limiting examples of augmentations which may be applied alone, or in combination, to medical images are shown in FIG. 3. Each of the plurality of augmented images may be fed to a trained machine learning model, and the machine learning model may map each augmented image to a corresponding segmentation mask, thereby producing a plurality of segmentation masks corresponding to the plurality of augmented images. The variation amongst the plurality of segmentation masks may be used to produce an uncertainty map, showing the spatial distribution of segmentation label variation in the plurality of segmentation masks. The segmentation label variation may correlate to an aleatoric uncertainty of the un-augmented input image. One embodiment of an uncertainty map is shown by uncertainty map 408 in FIG. 4. In some embodiments, the uncertainty maps produced herein may be used to automatically identify a least certain caliper placement, wherein the least certain caliper may be visually indicated and displayed to a user, along with a prompt for adjustment or confirmation of the caliper placement, as illustrated by the graphical user interface 500 shown in FIG. 5.

Referring to FIG. 1, an image processing system 100 is shown, in accordance with an exemplary embodiment. In some embodiments, image processing system 100 is incorporated into a medical imaging system. In some embodiments, at least a portion of image processing system 100 is disposed at a device (e.g., edge device, server, etc.) communicably coupled to a medical imaging system via wired and/or wireless connections. In some embodiments, at least a portion of image processing system 100 is disposed at a separate device (e.g., a workstation) which can receive images/maps from a medical imaging system or from a storage device which stores the images/data generated by the medical imaging system. Image processing system 100 may comprise a user input device 132, and display device 134.

Image processing system 100 includes a processor 104 configured to execute machine readable instructions stored in non-transitory memory 106. Processor 104 may be single core or multi-core, and the programs executed thereon may be configured for parallel or distributed processing. In some embodiments, the processor 104 may optionally include individual components that are distributed throughout two or more devices, which may be remotely located and/or configured for coordinated processing. In some embodiments, one or more aspects of the processor 104 may be virtualized and executed by remotely-accessible networked computing devices configured in a cloud computing configuration.

Non-transitory memory 106 may store machine learning module 108, augmentation module 110, and image data 112. machine learning module 108 may include one or more deep learning networks, comprising a plurality of weights and biases, activation functions, loss functions, gradient descent algorithms, and instructions for implementing the one or more machine learning models to process an input image. For example, machine learning module 108 may store instructions for pre-processing an image, and mapping the pre-processed image to a segmentation mask of a region of interest (ROI). machine learning module 108 may include trained and/or untrained neural networks and may further include training routines, or parameters (e.g., weights and biases), associated with one or more neural network models stored therein.

Non-transitory memory 106 may further include augmentation module 110, which may be configured to select an un-augmented or augmented image, and modify it by selecting and applying one or more modifications, such as is described in more detail in FIG. 3. In one example, augmentation module 110 is configured to select and apply a plurality of distinct augmentations to an input image to produce a plurality of distinctly augmented images.

Non-transitory memory 106 may further store image data 112, such as medical images captured by a medical imaging system. For example, image data 112 may store augmented and un-augmented medical images, and other types of medical image data.

In some embodiments, the non-transitory memory 106 may include components disposed at two or more devices, which may be remotely located and/or configured for coordinated processing. In some embodiments, one or more aspects of the non-transitory memory 106 may include remotely-accessible networked storage devices configured in a cloud computing configuration.

Image processing system 100 may further include user input device 132. User input device 132 may comprise one or more of a touchscreen, a keyboard, a mouse, a trackpad, a motion sensing camera, or other device configured to enable a user to interact with and manipulate data within image processing system 100. In one example, user input device 132 may enable a user to make a selection of an ultrasound image to use in training a machine learning model, or for further processing using a trained machine learning model.

Display device 134 may include one or more display devices utilizing virtually any type of technology. In some embodiments, display device 134 may comprise a computer monitor, and may display augmented and or un-augmented ultrasound images. Display device 134 may be combined with processor 104, non-transitory memory 106, and/or user input device 132 in a shared enclosure, or may be peripheral display devices and may comprise a monitor, touchscreen, projector, or other display device known in the art, which may enable a user to view ultrasound images produced by an ultrasound imaging system, and/or interact with various data stored in non-transitory memory 106.

Figure 2:
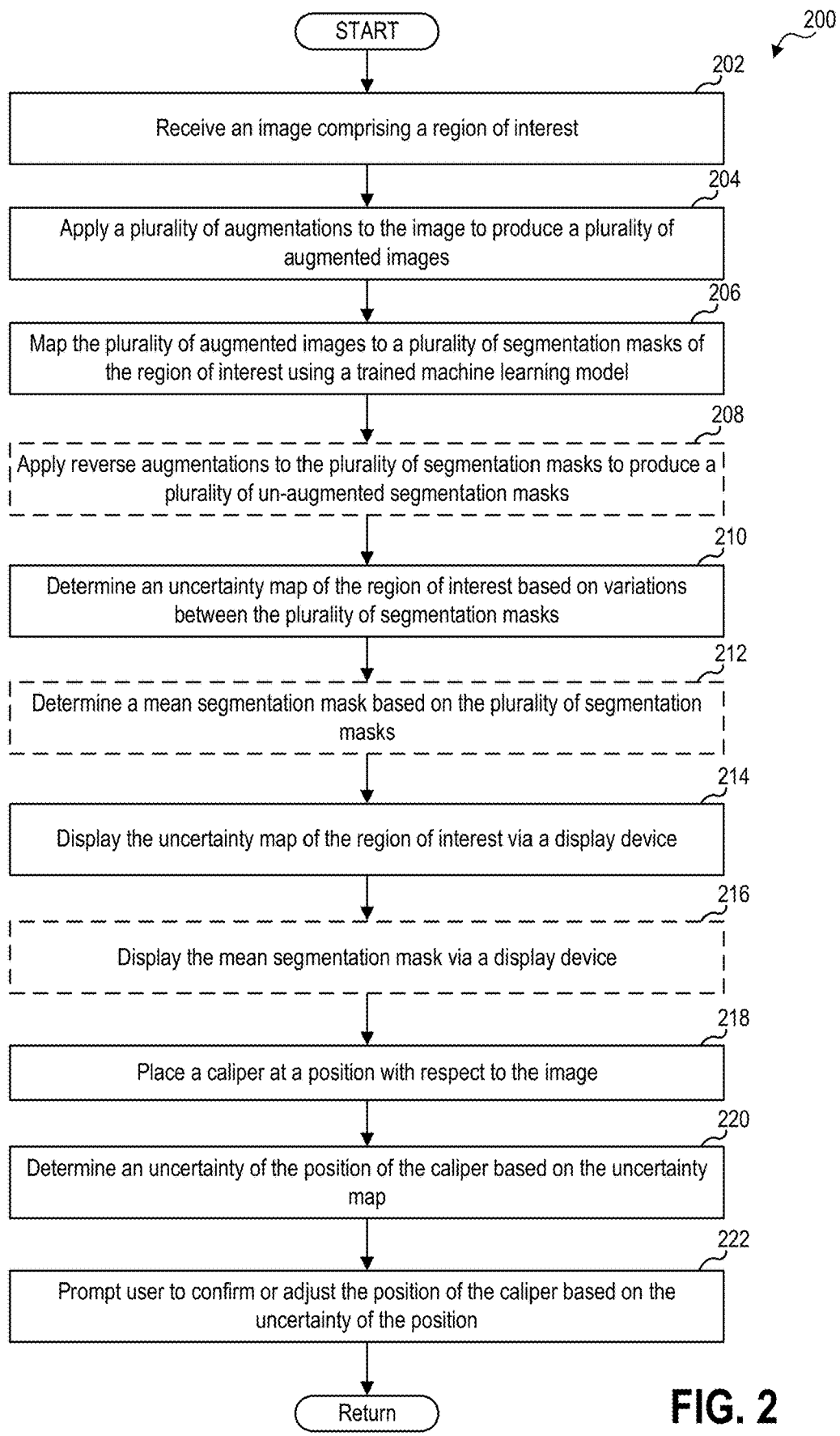
FIG. 2 is a flowchart illustrating a method for determining uncertainty in segmentation masks produced for a region of interest.
Figure 3:
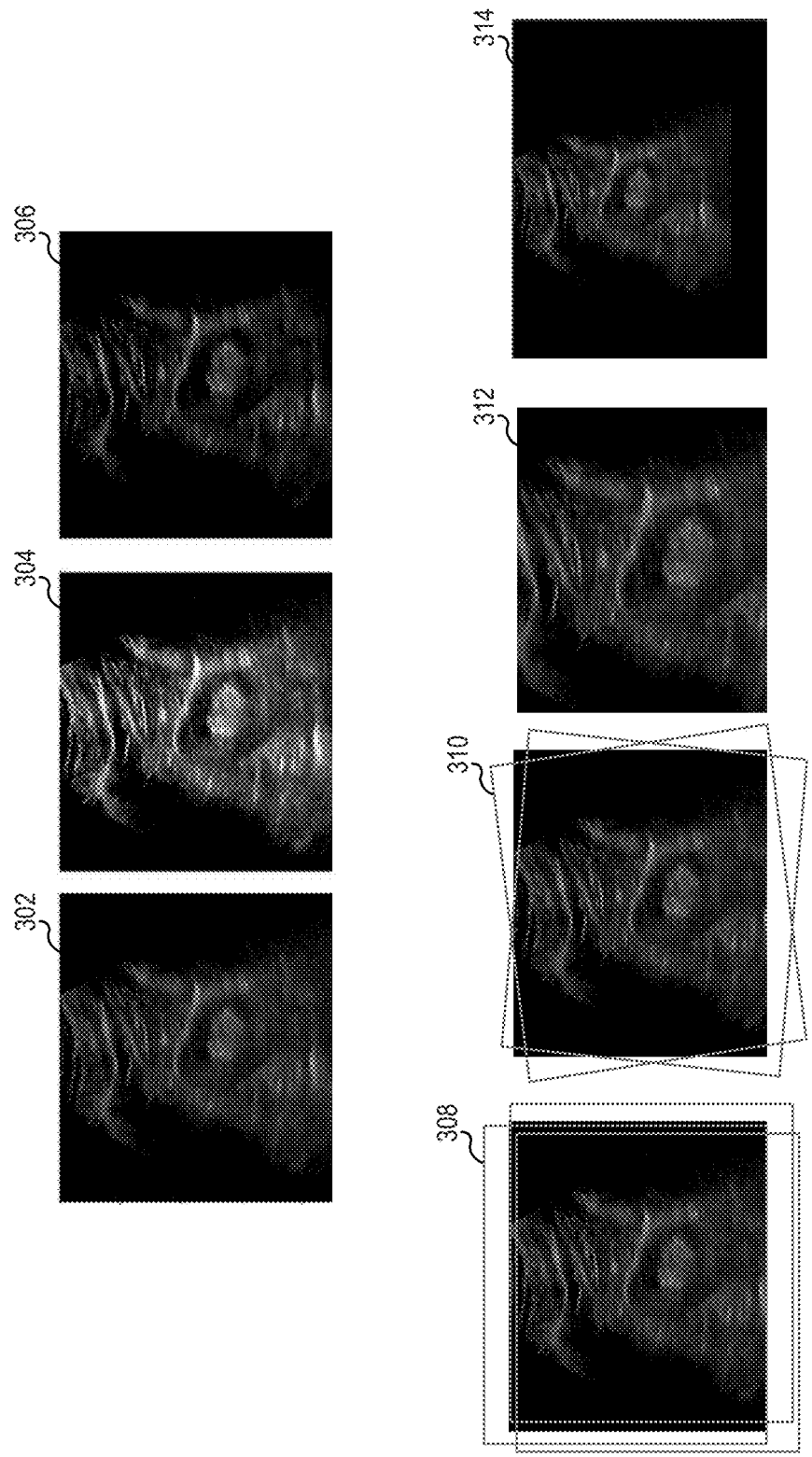
FIG. 3 shows example augmentations which may be applied to an input image to produce a plurality of augmented images.

It should be understood that image processing system 100 shown in FIG. 2 is for illustration, not for limitation. Another appropriate image processing system may include more, fewer, or different components.

Referring to FIG. 2, a flowchart of a method 200 for determining the uncertainty of a segmentation mask produced by a deep learning model is shown. Method 200 may be implemented by one or more of the above disclosed systems, such as image processing system 100.

Method 200 begins at operation 202, wherein the image processing system receives an image comprising a region of interest. In some embodiments, the image may include associated metadata, indicating an imaging modality used to acquire the image. One example of an image which may be received at operation 202 is shown by medical image 402 in FIG. 4. Image 402 is an ultrasound image of kidney, however it will be appreciated that the current disclosure may be applied to uncertainty determination in medical or non-medical images, and in medical images from a range of imaging modalities, including but not limited to MM, PET, CT, ultrasound, and x-ray.

At operation 204, the image processing system applies a plurality of augmentations to the image to produce a plurality of augmented images. In some embodiments, at operation 204, the image processing system determines a set of augmentations, applies the augmentations to the image received at operation 202 to generate an augmented image, and repeats this process N times to produce N distinctly augmented versions of the image received at operation 202, where N is a positive integer greater than 2. In some embodiments, the number of augmented images, N, produced at operation 202 is between 4 and 50. As described in more detail with reference to FIG. 3, augmentations applied at operation 204 may include one or more of a translation, rotation, zoom adjustment, simulated scanner depth adjustment, a simulated scanner gain adjustment, or augmentations specific to the modality of the image received at operation 202. Augmentations which introduce blur or noise into the image are not performed at operation 202, as this would skew the quantification of the uncertainty intrinsic to the image by artificially introducing additional uncertainty/noise.

Turning briefly to FIG. 3, a plurality of augmentations which may be applied at operation 204 are shown. Augmented images 302, 304, and 306, illustrate simulated receiver gain adjustments (simulated increase or decrease in receiver gain). Augmented image 308 illustrates translation augmentations (e.g., shifting the position via x, y, z translations). Augmented image 310 illustrates rotation augmentations. Augmented images 312 and 314 illustrate zoom adjustment augmentations (increased and decreased zoom, respectively). The augmentations applied to images 302, 304, and 306 may be considered as non-geometrical, as the mapping between pixels of between augmented and un-augmented images is not affected, whereas augmentations applied to images 308-314 are referred to as geometrical augmentations, as the mapping between augmented and un-augmented images is affected.

At operation 206, the image processing system maps the plurality of augmented images to a plurality of segmentation masks of the region of interest using a trained machine learning model. In some embodiments, each augmented image of the plurality of augmented images is fed through a machine learning model, wherein the machine learning model is trained to map images to segmentation masks of the region of interest, and thereby a plurality of segmentation masks derived from the image received at operation 202 are produced. In some embodiments, the trained machine learning model employed at operation 206 may comprise a convolutional neural network, although the current disclosure may be applied to substantially any machine learning model. One example of a single segmentation mask which may be produced at operation 206 is shown by segmentation mask 404 in FIG. 4, wherein pixels labeled as belonging to a region of interest 410 are shown in white.

At operation 208, the image processing system may optionally reverse the spatially distorting augmentations carried forward in the plurality of segmentation masks produced at operation 206. Not all augmentations are spatially distorting, however, in images augmented by geometric augmentations such as translation, rotation, cropping etc., the segmentation mask produced from said augmented image will also include the spatial distortions of the parent augmented image. The image processing system may reverse the augmentation by applying an opposite geometric augmentation at operation 208. As an example, if a parent augmented image is rotated by 33 degrees, and translated to the left by 14 pixels, the segmentation mask produced therefrom may be un-augmented by applying a −33 degree rotation and a 14 pixel translation to the right. It will be appreciated that the current disclosure provides for non-geometric/non-spatially distorting augmentations, such as contrast adjustment, scanner gain adjustment, etc., and as such augmentations do not alter a spatial mapping between points of the image received at operation 202 and the segmentation masks produced at operation 206, reverse augmentation at operation 208 may be bypassed.

At operation 210, the image processing system determines the uncertainty associated with the location and extent of the segmented region of interest in the plurality of segmentation masks. As no two images of the plurality of augmented images are identical, due to the distinct augmentations applied, the segmentation masks produced may show differences/variations in the predicted location and extent of the region of interest. Portions of the region of interest which show little or no variation amongst the plurality of segmentation masks are considered as more certain than portions of the region of interest which show greater variation. In other words, if a particular pixel of an input image is consistently classified as belonging to a region of interest (or not belonging to the region of interest), invariant of the augmentations applied to the input image, the pixel classification may be considered more certain (less uncertain) than a pixel for which the classification is highly augmentation dependent. Therefore, at operation 210, the image processing system may assess, for each corresponding point/pixel/voxel of the plurality of segmentation masks, a degree of segmentation label variation. In some embodiments, the variation may be determined as one or more of the range, standard deviation, or variance of the vector of values (segmentation labels) across each of the plurality of segmentation masks. As variation is assessed on a pixel-by-pixel basis (or voxel-by-voxel), the determination of uncertainty at operation 210 may be described as determining the pixel-wise variation of the segmentation labels across each of the plurality of segmentation masks. One example of an uncertainty map, such as may be produced at operation 210, is shown by uncertainty map 408 in FIG. 4. Lighter regions of uncertainty map 408 show regions greater segmentation label variation. As can be seen, the boundary of the region of interest is the region of greatest uncertainty, however all but the right portion of the boundary is only several pixels wide, indicating low uncertainty. Uncertainty map 408 clearly highlights that the right portion of the region of interest has a relatively uncertain boundary, as shown by the width of the boundary.

At operation 212, the image processing system may optionally determine a mean segmentation mask from the plurality of segmentation masks by taking the pixel-wise averages of segmentation labels at each corresponding pixel across the plurality of segmentation masks. One example of a mean segmentation mask which may be produced at operation 212 is shown by mean segmentation mask 404 in FIG. 4. In mean segmentation mask 406, the lighter region 412 indicates pixels classified as belonging to the region of interest, whereas darker regions indicate pixels not classified as belonging to the region of interest.

Figure 4:
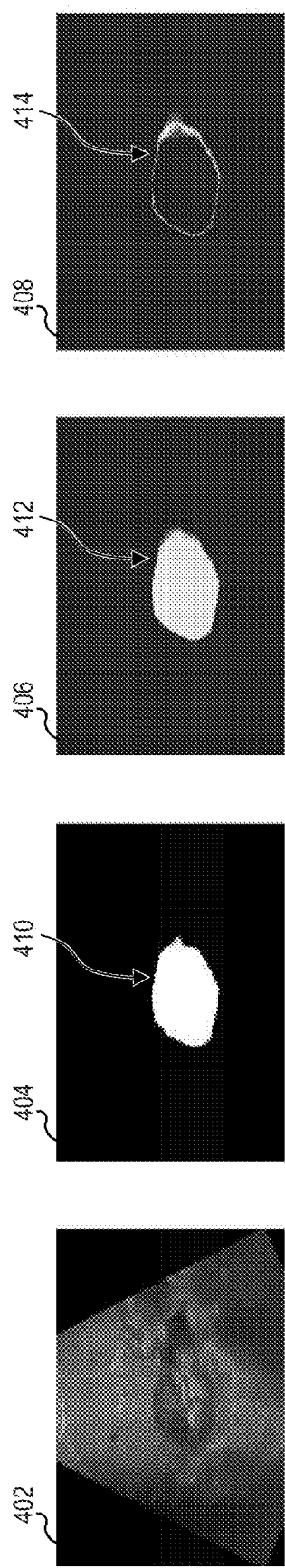
FIG. 4 shows a medical image including a region of interest, a segmentation mask of the region of interest, a mean segmentation mask of the region of interest, and an uncertainty map of the region of interest.
Figure 5:
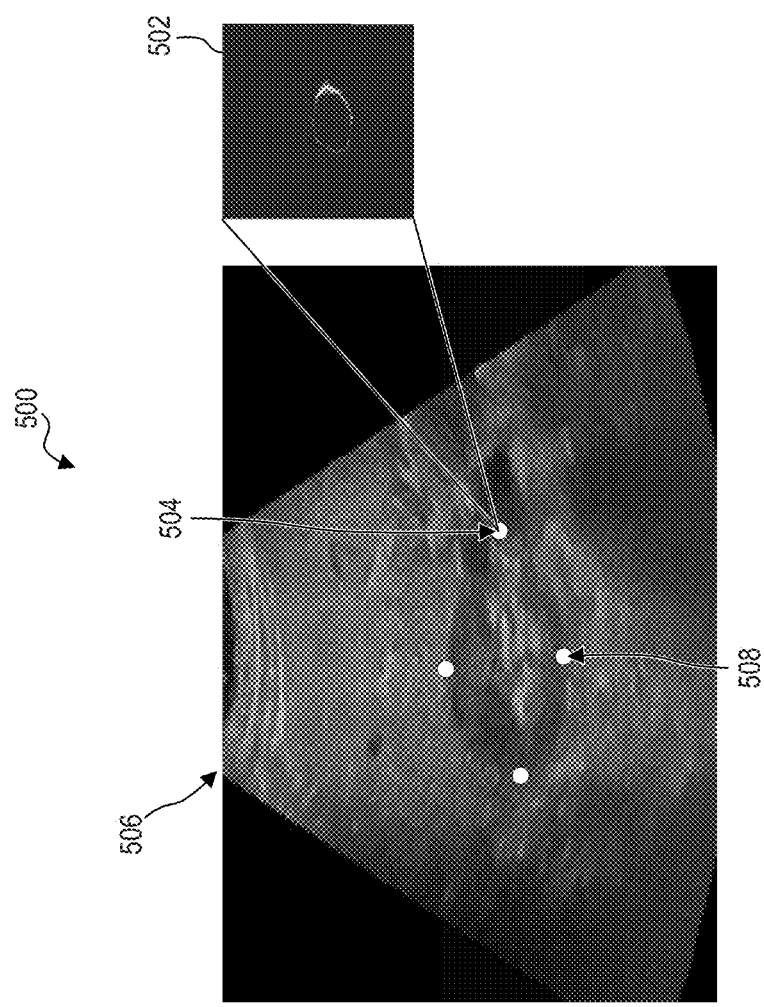
FIG. 5 shows an example graphical user interface including an uncertainty map.

At operation 214, the image processing system displays the uncertainty map produced at operation 210 via a display device. Turning briefly to FIG. 5, one example of a graphical user interface 500 which may be used to display the uncertainty map produced at operation 214, is shown. By displaying the uncertainty map, a user may be better informed of the consistency/invariability of the segmentation mask determined and, may be enabled to make a more informed decision regarding whether to accept or reject information derived therefrom. Turning briefly to FIG. 4, another example of an uncertainty map 408 is shown. Uncertainty map 408 shows the uncertainty associated with the segmented anatomical region of interest. In particular, uncertainty map 408 indicates regions of greater uncertainty/variability of segmentation labels for the anatomical region of interest in lighter colored regions, with darker colored regions indicating less segmentation uncertainty/variability. In particular, uncertainty map 408 shows the boundary 414 of the anatomical region of interest as a ring of lighter color, indicating greater segmentation label variability. Both the interior and exterior of the anatomical region of interest are dark, indicating a low uncertainty/variability of the segmentation labels assigned in each respective region. Contrastingly, the boundary 414 of the anatomical region of interest comprises relatively uncertain/variable segmentation labels, as indicated by the brighter coloring. In particular, the right portion of boundary 414 of the anatomical region of interest shows a relatively broad section of uncertainty/variability, whereas the left, top, and bottom portions of boundary 414 comprise relatively thin sections of uncertainty/variability. In other words, the left, top, and bottom portions of boundary 414 of the anatomical region of interest are sharply delineated by the segmentation labels, whereas the right portion of boundary 414 of the anatomical region of interest is less sharply delineated.

At operation 216, the image processing system may optionally display the mean segmentation mask produced at operation 212 via a display device. One example of a mean segmentation mask 404, showing a region of interest 410, is shown in FIG. 4. In mean segmentation mask 404, darker regions correspond to non-region of interest sub-regions of the input image 402 (e.g., sub-regions with segmentation labels indicating the sub-region is not a region of interest), and lighter regions correspond to sub-regions of input image 402 classified as belonging to the region of interest (e.g., sub-regions with segmentation labels indicating the sub-region is a region of interest). By showing the mean segmentation mask produced from the plurality of segmentation masks, a more accurate estimate of the position and extent of the region of interest may be produced, and conveyed to a user. In one example, a mean segmentation mask may better encode the aleatoric uncertainty of the segmentation labels (e.g., a prediction that a particular sub-region in an input image is part of a region of interest) for each respective position/pixel/voxel of an input image, as the segmentation labels for each sub-region of the segmentation mask is derived from a plurality of segmentation labels from a plurality of segmentation masks produced from a plurality of augmented versions of a same input image. A limitation of conventional approaches for determining a region of interest in an input image is reliance on a single segmentation mask, which does not reflect the aleatoric uncertainty of the input image, and may thus provide a false appearance of certainty.

At operation 218, the image processing system places a caliper at a position with respect to the input image. In some embodiments, calipers or other markers may be automatically positioned within an image based on a region of interest identified by a segmentation mask. In one example, the image processing system places the caliper within, or at the border of, the anatomical region of interest indicated by the plurality of segmentation masks produced at operation 206. In some embodiments, the image processing system may determine the position of the caliper based on the mean segmentation mask produced at operation 212. In some embodiments, the position may be determined relative to the segmented region of interest, e.g., the position of the caliper may be placed at a center point of a region of interest, at an edge/border of the region of interest, or at a pre-determined relative location with respect to the region of interest (e.g., at a point a pre-determined relative distance along a major axis of a segmented region of interest as determined by principal component analysis, at a point a pre-determined relative distance, such as 40%, along a first minor axis of the segmented region of interest, etc.). In one example, calipers may be placed to indicate anatomical landmarks, which may be informative to a user. In another example, calipers may be placed as part of a measuring process, wherein one or more dimensions of the anatomical region of interest are to be measured. In one example, one or more of a volume, area, height, width, or depth, of an anatomical region of interest may be determined based on the position of one or more calipers using methods known in the art of medical image analysis. In another example, calipers may be placed to determine the orientation/position of a scanning device relative to an anatomical region of interest.

At operation 220, the image processing system determines an uncertainty of the position of the caliper based on the uncertainty map. In one example, the image processing system may determine the uncertainty of the position of the caliper by determining a plurality of uncertainty values in a region proximal to, and including, the position of the caliper, wherein the plurality of uncertainty values are obtained by accessing uncertainty values from locations of the uncertainty map corresponding to the region proximal to, and including, the position of the caliper. In one example, the plurality of uncertainty values proximal to the position of the caliper are averaged to produce an uncertainty of the position of the caliper. In some embodiments, the uncertainty of the position of the caliper is determined by summing the plurality of uncertainty values to produce the uncertainty of the position of the caliper. In some embodiments, uncertainty values are sampled from points in the uncertainty map within a pre-determined radius of the position of the caliper. In some embodiments, an uncertainty of a caliper placement may be determined based on averaging the uncertainty values in a pre-determined radius of the caliper position, wherein the uncertainty values are obtained from the uncertainty map produced at operation 210. In some embodiments, uncertainty values obtained from the uncertainty map may be combined according to a weighting scheme, to produce the uncertainty of the position of the caliper. In one example, uncertainty values from the uncertainty map may be weighted based on a distance from the current position of the caliper. In some embodiments, a weighting of an uncertainty value may be inversely proportional to a distance of the uncertainty value from the position of the caliper.

At operation 222, the image processing system may prompt a user to confirm or adjust the position of the caliper based on the uncertainty of the position of the caliper determined at operation 220. In some embodiments, in response to the uncertainty determined at operation 220 exceeding an uncertainty threshold, the image processing system may prompt a user to confirm or adjust the position of the caliper. In some embodiments, the prompt may comprise displaying the position of the caliper overlaid on the input image. In some embodiments, the prompt may comprise displaying the position of the caliper overlaid on a mean segmentation mask. In some embodiments, the prompt may comprise displaying the position of the caliper overlaid on the uncertainty map. The prompt may further include selectable interface elements for confirming or adjusting, the position of the caliper, respectively. In conventional approaches a user would assess the placement of each caliper and either confirm, or adjust the caliper positions in order to perform an anatomical measurement, e.g., a volume or area estimation of the anatomical region of interest. However, the current disclosure enables a more efficient workflow, by automatically highlighting or emphasizing caliper positions with greater than a threshold uncertainty, thereby enabling a user to quickly determine which caliper placements may benefit from critical evaluation/adjustment, and which caliper placements are acceptable. In some embodiments, calipers/markers with greater than a pre-determined threshold of uncertainty may be flagged and/or highlighted in a graphical user interface, such as graphical user interface 500 shown in FIG. 5.

In response to a user selecting to adjust the position of the caliper, the image processing system may prompt the user to input an updated position of the caliper using a user input device. Responsive to receiving user input of an updated caliper position, the image processing system may display the updated caliper position via a display device. Alternatively, in response to a user selecting to confirm the position of the caliper, the image processing system may determining an anatomical measurement based on the position of the caliper, and display the anatomical measurement via the display device.

In some examples, if at operation 222, the caliper does not exceed the pre-determined uncertainty threshold, the image processing system may automatically conduct the anatomical measurement based on the caliper position, and output the result of the anatomical measurement via a display device.

Following operation 222, method 200 may end. In this way, the uncertainty of the location and extent of a segmented region of interest may be quantified, and intuitively graphically presented to a user, thereby enabling the user to make a more informed decision whether to accept or reject the information presented based on the segmented region of interest. Further, by automatically highlighting caliper placements with greater than a threshold uncertainty, increased efficiency in medical image analysis may be enabled, as a radiologist or technician may be enabled to easily select and adjust calipers positions of greater than a threshold uncertainty. Further, method 200 includes bypassing manual inspection of caliper positions with lower than a threshold uncertainty, thereby streamlining a manual assessment portion of an anatomical measurement workflow.

Turning to FIG. 5, one example of a graphical user interface (GUI) 500 is shown. GUI 500 illustrates one example of how a position of a caliper with greater than a threshold uncertainty may be automatically presented to a user, such as is described at operation 222 of method 200. GUI 500 includes a highlighted caliper 504, along with an un-highlighted caliper 508, overlaid on a medical image 506. Each of caliper 504 and caliper 508 are positioned along an outer boundary of an anatomical region of interest captured by the medical image 506. In one example, caliper 504 and caliper 508 may be used to automatically determine an area or volume of the anatomical region of interest.

GUI 500 further includes an uncertainty map 502, showing the uncertainty associated with the segmented anatomical region of interest. In particular, uncertainty map 502 indicates higher uncertainty/variability of segmentation labels for the anatomical region of interest in lighter colored regions, with darker colored regions indicating lower segmentation uncertainty/variability. As can be seen, the interior and exterior of the anatomical region of interest are dark, indicating a low uncertainty/variability of the segmentation labels assigned in each respective region. Contrastingly, the boundary of the anatomical region of interest comprises relatively uncertain/variable segmentation labels, as indicated by the brighter coloring. In particular, the right boundary of the anatomical region of interest shows a relatively broad region of uncertainty/variability, whereas the left, top, and bottom boundaries comprise relatively thin regions of uncertainty/variability. In other words, the left, top, and bottom boundaries of the anatomical region of interest are sharply delineated by the segmentation labels, whereas the right boundary of the anatomical region of interest is less sharply delineated. The current position of highlighted caliper 504 is proximal to/within the right region of uncertainty/variability, as indicated by uncertainty map 502. In other words, the position of caliper 504 is less certain than caliper 508 as the uncertainty values proximal to and including the position of caliper 504 are greater than the uncertainty values proximal to and including the position of caliper 508. By displaying the uncertainty map 502, along with an indication of the position of caliper 504 with respect to the uncertainty map 502, a user may be clearly informed of the uncertainty associated with the current position of caliper 504, as well as provided with information as to the spatial extent and the degree of the segmentation label variation throughout the image 506, and particularly in the region proximal to the current position of caliper 504.

The disclosure also provides support for a method comprising: receiving an image including a region of interest, applying a plurality of augmentations to the image to produce a plurality of augmented images, feeding each of the plurality of augmented images to a trained machine learning model to produce a plurality of segmentation masks of the region of interest, determining an uncertainty of a location and extent of the region of interest based on variations between the plurality of segmentation masks, and displaying the uncertainty of the location and extent of the region of interest via a display device. In a first example of the method, determining the uncertainty of the location and extent of the region of interest based on variations between the plurality of segmentation masks comprises: determining a pixel-wise variation between each of the plurality of segmentation masks, and generating an uncertainty map showing the pixel-wise variation of the region of interest. In a second example of the method, optionally including the first example, determining the pixel-wise variation between each of the plurality of segmentation masks comprises: applying to each of the plurality of segmentation masks a reverse augmentation to produce a plurality of un-augmented segmentation masks, wherein the reverse augmentation applied to a particular segmentation mask reverses a spatial distortion applied to produce the augmented image from which the particular segmentation mask was produced, and determining segmentation label variation across each corresponding pixel of the plurality of un-augmented segmentation masks, wherein the uncertainty map shows the segmentation label variation for each pixel of the image. In a third example of the method, optionally including one or both of the first and second examples, the variation comprises one or more of a standard deviation, a range, and a variance, of numerical labels applied to each pixel of the image. In a fourth example of the method, optionally including one or more each of the first through third examples the method further comprising: determining a mean segmentation mask based on the plurality of segmentation masks by taking pixel-wise averages across spatially corresponding pixels from the plurality of segmentation masks. In a fifth example of the method, optionally including one or more or each of the first through fourth examples, the image is a medical image, and wherein the region of interest is an anatomical region of interest captured by the medical image. In a sixth example of the method, optionally including one or more or each of the first through fifth examples, applying the plurality of augmentations to the image to produce the plurality of augmented images comprises applying one or more of a translation, rotation, zoom adjustment, or contrast adjustment, to the image, and wherein no two augmented images of the plurality of augmented images are identical. In a seventh example of the method, optionally including one or more or each of the first through sixth examples, a number of the plurality of augmented images is between 4 and 50 images. In a eighth example of the method, optionally including one or more or each of the first through seventh examples the method further comprising: placing a caliper at a position within the image based on the plurality of segmentation masks, determining an uncertainty of the position of the caliper based on the uncertainty of the location and extent of the region of interest, and responding to the uncertainty of the position of the caliper being greater than a pre-determined threshold by: displaying a visual indication of the position of the caliper via a display device, and prompting a user to confirm or edit the position of the caliper.

The disclosure also provides support for a method comprising: receiving a medical image including an anatomical region of interest, applying a plurality of augmentations to the medical image to produce a plurality of augmented images, feeding each of the plurality of augmented images to a trained machine learning model to produce a plurality of segmentation masks of the anatomical region of interest, determining a mean segmentation mask of the anatomical region of interest from the plurality of segmentation masks, determining pixel-wise variation of segmentation labels across the plurality of segmentation masks to produce an uncertainty map of the region of interest, displaying the mean segmentation mask and the uncertainty map via a display device. In a first example of the method the method further comprising: placing a caliper at a position within the medical image based on the mean segmentation mask, determining an uncertainty of the position of the caliper based on the uncertainty map, and responding to the uncertainty of the position of the caliper exceeding a pre-determined uncertainty threshold by: automatically displaying the position of the caliper overlaid on the medical image, and prompting a user to confirm or adjust the position of the caliper. In a second example of the method, optionally including the first example, determining the uncertainty of the position of the caliper based on the uncertainty map comprises: determining a plurality of uncertainty values in a region proximal to, and including, the position of the caliper, wherein the plurality of uncertainty values are obtained by accessing locations of the uncertainty map corresponding to the region proximal to, and including, the position of the caliper. In a third example of the method, optionally including one or both of the first and second examples the method further comprising: averaging the plurality of uncertainty values to determine the uncertainty of the position of the caliper. In a fourth example of the method, optionally including one or more or each of the first through third examples, the region is a circular or spherical region centered on the position of the caliper, and wherein the circular or spherical region is of a pre-determined radius. In a fifth example of the method, optionally including one or more or each of the first through fourth examples, the position of the caliper is a pre-determined location relative to the anatomical region of interest.

The disclosure also provides support for a system for determining uncertainty in a segmented region of interest comprising: a memory, wherein the memory stores instructions, a trained machine learning model, and an augmentation module, a display device, and a processor communicably coupled to the memory and the display device, wherein, when executing the instructions, the processor is configured to: receive a medical image including an anatomical region of interest, feed the medical image to the augmentation module, wherein a plurality of augmentations are applied to the medical image to produce a plurality of augmented images, map the plurality of augmented images to a plurality of segmentation masks of the anatomical region of interest using the trained machine learning model, determine pixel-wise variations of segmentation labels across the plurality of segmentation masks to produce an uncertainty map of the anatomical region of interest, and display the uncertainty map via the display device. In a first example of the system when executing the instructions, the processor is further configured to: place a caliper at a position within the anatomical region of interest, determine an uncertainty of the position of the caliper based on the uncertainty map, and respond to the uncertainty of the position of the caliper exceeding a pre-determined uncertainty threshold by automatically displaying the position of the caliper overlaid on the medical image, and prompting a user to confirm or adjust the position of the caliper. In a second example of the system, optionally including the first example, the system further comprises a user input device communicably coupled to the processor, and wherein, when executing the instructions, the processor is further configured to: receive a user input specifying an updated position of the caliper, and display the updated position of the caliper overlaid on the medical image. In a third example of the system, optionally including one or both of the first and second examples, the processor is configured to determine the uncertainty of the position of the caliper based on the uncertainty map by: determining a plurality of uncertainty values in a region proximal to, and including, the position of the caliper, wherein the plurality of uncertainty values are obtained by accessing locations of the uncertainty map corresponding to the region proximal to, and including, the position of the caliper, and summing the plurality of uncertainty values to produce the uncertainty of the position of the caliper. In a fourth example of the system, optionally including one or more or each of the first through third examples when executing the instructions, the processor is further configured to: determine a mean segmentation mask from the plurality of segmentation masks, place a caliper at a position within the mean segmentation mask of the anatomical region of interest, determine an uncertainty of the position of the caliper based on the uncertainty map, and respond to the uncertainty of the position of the caliper not exceeding a pre-determined uncertainty threshold by: automatically determining an anatomical measurement based on the position of the caliper, and displaying the anatomical measurement via the display device.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising,"

"including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method comprising:
receiving an image including a region of interest;
determining a segmentation mask for the region of interest using a trained machine learning model;
placing a caliper at a position within the image based on the segmentation mask;
determining an uncertainty of the position of the caliper based on an uncertainty of the segmentation mask, wherein the uncertainty of the segmentation mask is determined by:
applying a plurality of augmentations to the image to produce a plurality of augmented images;
feeding each of the plurality of augmented images to the trained machine learning model to produce a plurality of segmentation masks of the region of interest; and
determining the uncertainty of the segmentation mask based on variations between the plurality of segmentation masks by:
applying to each of the plurality of segmentation masks a reverse augmentation to produce a plurality of un-augmented segmentation masks, and determining segmentation label variation across each corresponding pixel of the plurality of un-augmented segmentation masks to determine a pixel-wise variation between each of the plurality of segmentation masks; and
responding to the uncertainty of the position of the caliper being greater than a pre-determined threshold by:
displaying a visual indication of the position of the caliper via a display device; and
prompting a user to confirm or edit the position of the caliper.

2. The method of claim 1, wherein the pixel-wise variation comprises one or more of a standard deviation, a range, and a variance, of segmentation labels applied to each pixel of the image.

3. The method of claim 1, wherein the segmentation mask is a mean segmentation mask produced by averaging the plurality of segmentation masks.

4. The method of claim 1, wherein the image is a medical image, and wherein the region of interest is an anatomical region of interest captured by the medical image.

5. The method of claim 1, wherein applying the plurality of augmentations to the image to produce the plurality of augmented images comprises applying one or more of a translation, rotation, zoom adjustment, or contrast adjustment, to the image, and wherein no two augmented images of the plurality of augmented images are identical.

6. The method of claim 1, wherein a number of the plurality of augmented images is between 4 and 50 images.

7. A method comprising:
receiving a medical image including an anatomical region of interest;
applying a plurality of augmentations to the medical image to produce a plurality of augmented images;
feeding each of the plurality of augmented images to a trained machine learning model to produce a plurality of segmentation masks of the anatomical region of interest;
determining a mean segmentation mask of the anatomical region of interest from the plurality of segmentation masks;
determining pixel-wise variation of segmentation labels across the plurality of segmentation masks to produce an uncertainty map of the anatomical region of interest;
placing a caliper at a position within the medical image based on the mean segmentation mask;
determining an uncertainty of the position of the caliper based on the uncertainty map by determining a plurality of uncertainty values in a region proximal to, and including, the position of the caliper, wherein the plurality of uncertainty values are obtained by accessing locations of the uncertainty map corresponding to the region proximal to, and including, the position of the caliper; and
determining the uncertainty of the position of the caliper based on an average of the plurality of uncertainty values.

8. The method of claim 7, the method further comprising:
responding to the uncertainty of the position of the caliper exceeding a pre-determined uncertainty threshold by:
automatically displaying the position of the caliper overlaid on the medical image; and
prompting a user to confirm or adjust the position of the caliper.

9. The method of claim 8, wherein the position of the caliper is a pre-determined location relative to the anatomical region of interest.

10. The method of claim 7, wherein the plurality of uncertainty values are accessed from locations of the uncertainty map within a pre-determined radius of the position of the caliper.

11. A system for determining uncertainty in a segmented region of interest comprising:
a memory, wherein the memory stores instructions, a trained machine learning model, and an augmentation module;
a display device; and
a processor communicably coupled to the memory and the display device, wherein, when executing the instructions, the processor is configured to:
receive a medical image including an anatomical region of interest;

feed the medical image to the augmentation module, wherein a plurality of augmentations are applied to the medical image to produce a plurality of augmented images;

map the plurality of augmented images to a plurality of segmentation masks of the anatomical region of interest using the trained machine learning model;

determine pixel-wise variations of segmentation labels across the plurality of segmentation masks to produce an uncertainty map of the anatomical region of interest;

place a caliper at a position within the anatomical region of interest;

determine an uncertainty of the position of the caliper based on the uncertainty map by:
- determining a plurality of uncertainty values in a region proximal to, and including, the position of the caliper, wherein the plurality of uncertainty values are obtained by accessing locations of the uncertainty map corresponding to the region proximal to, and including, the position of the caliper; and
- summing the plurality of uncertainty values to produce the uncertainty of the position of the caliper and respond to the uncertainty of the position of the caliper exceeding a pre-determined uncertainty threshold by:
- automatically displaying the position of the caliper overlaid on the medical image; and
- prompting a user to confirm or adjust the position of the caliper.

12. The system of claim 11, wherein the system further comprises a user input device communicably coupled to the processor, and wherein, when executing the instructions, the processor is further configured to:
- receive a user input specifying an updated position of the caliper; and
- display the updated position of the caliper overlaid on the medical image.

13. The system of claim 11, wherein, when executing the instructions, the processor is further configured to:
- determine a mean segmentation mask from the plurality of segmentation masks;
- place a caliper at a position within the mean segmentation mask of the anatomical region of interest;
- determine an uncertainty of the position of the caliper based on the uncertainty map; and
- respond to the uncertainty of the position of the caliper not exceeding a pre-determined uncertainty threshold by:
  - automatically determining an anatomical measurement based on the position of the caliper; and
  - displaying the anatomical measurement via the display device.

* * * * *